(12) United States Patent
Capanna et al.

(10) Patent No.: US 11,911,275 B2
(45) Date of Patent: Feb. 27, 2024

(54) ACTIVE SUBSTANCE APPLICATOR FOR A JOINT IMPLANT, AND JOINT IMPLANT HAVING AN ACTIVE SUBSTANCE APPLICATOR

(71) Applicant: Waldemar Link GmbH & Co. KG, Hamburg (DE)

(72) Inventors: Rodolfo Capanna, Florence (IT); Helmut D. Link, Hamburg (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 26 days.

(21) Appl. No.: 17/041,351

(22) PCT Filed: Mar. 19, 2019

(86) PCT No.: PCT/EP2019/056802
§ 371 (c)(1),
(2) Date: Sep. 24, 2020

(87) PCT Pub. No.: WO2019/185398
PCT Pub. Date: Oct. 3, 2019

(65) Prior Publication Data
US 2021/0093455 A1    Apr. 1, 2021

(30) Foreign Application Priority Data

Mar. 26, 2018  (EP) .................................. 18163947

(51) Int. Cl.
*A61F 2/30* (2006.01)
*A61L 27/54* (2006.01)
*A61F 2/38* (2006.01)

(52) U.S. Cl.
CPC .......... *A61F 2/30721* (2013.01); *A61L 27/54* (2013.01); *A61F 2002/30331* (2013.01);
(Continued)

(58) Field of Classification Search
CPC ................ A61F 2/30721; A61F 2/3859; A61F 2002/30331; A61F 2002/3068;
(Continued)

(56) References Cited

U.S. PATENT DOCUMENTS

| 5,002,578 A | * | 3/1991 | Luman | ...................... A61F 2/36 623/22.42 |
| 5,108,452 A | * | 4/1992 | DeMane | ............. A61F 2/30734 623/22.42 |

(Continued)

FOREIGN PATENT DOCUMENTS

| EP | 0 244 720 A1 | 11/1987 |
| EP | 2 052 700 A1 | 4/2009 |
| EP | 2328511 A2 | 6/2011 |

OTHER PUBLICATIONS

International Search Report and Written Opinion dated May 20, 2019 in corresponding International Application No. PCT/EP2019/056802.

*Primary Examiner* — Brian A Dukert
*Assistant Examiner* — Melissa A Hoban
(74) *Attorney, Agent, or Firm* — Chiesa Shahinian & Giantomasi PC

(57) ABSTRACT

The present invention provides an active substance application insert (10, 110) for an implant (30), in particular a joint implant. The active substance application insert has a main body (11), an active substance chamber (12) formed in the main body, an application side (13, 113) which forms a front face of the active substance chamber, wherein the application side has a plurality of application openings (14, 114), and a securing means (15) with which the main body can be detachably secured in the implant. In a state in which the main body is inserted into the implant, the application side faces outwards relative to the implant, such that the application openings connect the active substance chamber to the
(Continued)

environment of the implant. Furthermore, within the scope of the present invention an implant (30) with a recess (31) for receiving an active substance application insert (10, 110) is provided.

14 Claims, 2 Drawing Sheets

(52) U.S. Cl.
CPC ..... *A61F 2002/3068* (2013.01); *A61F 2/3859* (2013.01); *A61L 2430/24* (2013.01)

(58) Field of Classification Search
CPC .. A61F 2002/30677; A61F 2002/30772; A61F 2/30744; A61F 2002/30604; A61F 2002/30672; A61F 2002/30784; A61L 27/54; A61L 2430/24
See application file for complete search history.

(56) References Cited

U.S. PATENT DOCUMENTS

| | | | | |
|---|---|---|---|---|
| 5,330,536 A * | 7/1994 | Tager | A61F 2/3662 | 623/23.33 |
| 5,681,289 A * | 10/1997 | Wilcox | A61F 2/32 | 606/62 |
| 5,776,199 A * | 7/1998 | Michelson | A61F 2/30744 | 606/247 |
| 5,800,557 A * | 9/1998 | Elhami | A61B 17/1753 | 623/23.12 |
| 5,888,208 A * | 3/1999 | Ro | A61F 2/4684 | 623/23.15 |
| 6,607,560 B1 * | 8/2003 | Pfaff | A61F 2/30965 | 623/22.45 |
| 7,156,880 B2 * | 1/2007 | Evans | A61P 19/02 | 623/23.51 |
| 8,080,059 B2 * | 12/2011 | Fell | A61F 2/3872 | 623/14.12 |
| 8,377,062 B2 * | 2/2013 | Lutz | A61B 17/72 | 606/62 |
| 9,278,002 B2 * | 3/2016 | Merrell | A61F 2/3804 | |
| 9,642,658 B2 * | 5/2017 | Boyd | A61B 17/7061 | |
| 9,700,431 B2 * | 7/2017 | Nebosky | A61F 2/3094 | |
| RE46,669 E * | 1/2018 | de Beaubien | A61F 2/36 | |
| 10,022,233 B1 * | 7/2018 | Gall | A61F 2/3859 | |
| 10,350,332 B2 * | 7/2019 | Stalcup | A61B 17/846 | |
| 2001/0051831 A1 * | 12/2001 | Subba Rao | A61F 2/3609 | 623/22.42 |
| 2002/0007220 A1 * | 1/2002 | Gie | A61F 2/3662 | 623/23.15 |
| 2002/0107520 A1 * | 8/2002 | Hoffman | A61B 17/15 | 623/23.11 |
| 2002/0169507 A1 * | 11/2002 | Malone | A61B 17/7064 | 623/17.11 |
| 2003/0187513 A1 * | 10/2003 | Durniak | A61B 17/8802 | 623/22.12 |
| 2004/0180072 A1 | 9/2004 | Tunc et al. | | |
| 2006/0093646 A1 * | 5/2006 | Cima | A61C 19/063 | 424/425 |
| 2007/0016163 A1 * | 1/2007 | Santini | A61L 28/0026 | 604/500 |
| 2008/0167723 A1 * | 7/2008 | Acker | A61F 2/3662 | 623/22.4 |
| 2009/0130167 A1 * | 5/2009 | Shelton | A61F 2/30721 | 424/423 |
| 2009/0281632 A1 * | 11/2009 | Naidu | A61F 2/4637 | 623/20.11 |
| 2010/0042214 A1 | 2/2010 | Nebosky et al. | | |
| 2013/0123742 A1 * | 5/2013 | Lin | A61P 19/02 | 604/500 |
| 2015/0250598 A1 | 9/2015 | Yakimicki et al. | | |
| 2020/0253739 A1 * | 8/2020 | Ishiwata | A61F 2/30771 | |

* cited by examiner

ACTIVE SUBSTANCE APPLICATOR FOR A JOINT IMPLANT, AND JOINT IMPLANT HAVING AN ACTIVE SUBSTANCE APPLICATOR

CROSS-REFERENCE TO RELATED APPLICATIONS

This application is the National Stage entry under 35 U.S.C. § 371 of International Application No. PCT/EP2019/056802 filed on Mar. 19, 2019, published on Oct. 3, 2019 under Publication Number WO 2019/185398 A1, which claims the benefit of priority under 35 U.S.C. § 119 of European Patent Application Number 18163947.7 filed on Mar. 26, 2018, the entireties of which are herein incorporated by reference.

FIELD OF THE INVENTION

The patent relates to an active substance application insert for an implant, in particular a joint implant, and an implant having such an active substance application insert.

PRIOR ART

In the case of joint implants, particularly in the case of a complete knee joint replacement, the size of these implants makes implantation a relatively major procedure. As a consequence, in the case of such a procedure an implant having a correspondingly large surface area is inserted into the body of a patient. This implant surface area is exposed to the environment outside the patient prior to implantation. For this reason alone, it is not possible to guarantee absolute sterility at the site of intervention, which would be required in order to be able to preclude periprosthetic infections with almost absolute certainty. In addition to hygienic risk factors there are also patient-specific risk factors that could promote a periprosthetic infection.

If such a periprosthetic infection does occur, it will generally be treated by administering active substances, in particular antibiotics. Particularly in the case of high-risk patients, such a treatment can also be carried out preventatively. The active substances are released right at the site of implantation. Collagen sponges, non-wovens or chains with bone cement beads, for example, which contain an active substance that is gradually released to fight or prevent inflammation, are used for this.

In the case of other administration techniques, the active substance is guided to the joint from the outside via infusion tubes and is administered there at the joint. Additional implants carrying an active substance can also be implanted. These implants have recesses on their surfaces, into which an active substance is introduced. The active substance is then gradually released in the implanted state in the body. EP 2 052 700 A1, for example, discloses an active substance delivery implant which is implanted together with a joint endoprosthesis and which has such recesses containing an active substance.

If the infection is not supressed by a single administration of active substances, it may be necessary to remove a part of or even the whole of the implant again. This results in the patient being substantially immobilised, however. To avoid this, placeholder implants can be inserted in place of the removed implant. These include implant imitations made of bone cement, for example, wherein the bone cement is also enriched with an active substance. Using such placeholder implants is an attempt to counter soft tissue contracture, muscular atrophy and bone weakening due to immobilisation. This is only possible to a limited extent, however.

Alternatively, there are implants in which active substance recesses are provided right from the beginning. For instance, U.S. Pat. No. 4,919,666 A discloses a hip endoprosthesis and an acetabulum in which pockets are provided which also contain an active substance at the time of implantation. To the same end, US 2004/0180072 A1 proposes individual comparatively large blind holes in implants to supply the joint with active substances.

In this case, however, the problem arises that once implanted, the release of the active substance can no longer be stopped. Moreover, the active substance cannot be changed, since it is encapsulated in an absorbable substance in the active substance recesses, i.e. it fills them. Yet both may be necessary if the patient demonstrates hypersensitivity to the active substance. As a consequence, it may be necessary to explant the implant again since the active substance cannot be removed, let alone be changed, in any other way. Moreover, the efficacy of the active substances used is subject to a limited stability.

All of this makes producing, holding available and storing implants with integrated active substances complicated and therefore cumbersome. Furthermore, active substance recesses may have the disadvantage that they leave depressions in the surface of the implant after the release of the active substance. These recesses are not suitable for the ingrowth of surrounding tissue due to their function of holding available a sufficiently large amount of active substances. Particularly if the depressions are in a region that comes into contact with bone tissue, the tissue does not grow in. As a consequence, the surface of these recesses is not available for anchoring the implant. If these recesses are in a region of the implant that comes into contact with soft tissue, there may also be complications on account of the residual recesses. One example of this is a local accumulation of fibrous tissue, which can adversely affect the function of the joint.

SUMMARY OF THE INVENTION

Against this background, an object of the present invention was to provide an active substance application insert with which it is possible not only to apply an active substance but also to change an active substance or to interrupt the release of an active substance in a targeted manner. In addition, the number of interventions to administer the active substance is to be kept to a minimum.

In view of these objects, the invention provides an active substance application insert for an implant, in particular a joint implant. The active substance application insert comprises a main body, an active substance chamber formed in the main body and an application side. The application side forms a front face of the active substance chamber, wherein the application side has a plurality of application openings. Moreover, the active substance application insert comprises a securing means with which the main body can be detachably secured in the implant. In a state in which the main body is inserted into the implant, the application side faces outwards relative to the implant, such that the application openings connect the active substance chamber to the environment of the implant.

With this design, the active substance application insert is a part of the implant that can be integrated into the joint implant. Thus, the active substance application insert is an additional part which is implanted without taking up additional space at the site of implantation.

Furthermore, the securing means makes it possible to remove an active substance application insert again once inserted, in order to top up, change or remove the active substance, for example. This is particularly advantageous in the case of patients developing sensitivity to the active substance, since an explantation can be thereby avoided.

Moreover, the placement of the active substance application insert directly in the implant ensures that the active substance contained in the active substance chamber is released directly into the periprosthetic environment. This can prevent, in particular, a biofilm on the surface of the implant, which can promote the development of an infection due to the protective effect thereof for pathogens.

In the inserted state, the outward-facing application side with application openings formed therein forms at least one part of the outer surface of the implant. The application side formed as a front wall is preferably flush with the outer side of the implant. More preferably still, it conforms geometrically to the external appearance of the implant, i.e. to the contour thereof.

In a preferred embodiment, a rear wall is formed on the side opposite the application side, which forms a rear face of the active substance chamber and which faces the implant in the inserted state.

If the active substance chamber has a rear wall, the active substance chamber is a closed space, except for the application openings. Thus, the active substance can only escape via the application openings.

In a further preferred embodiment, at least one section of the rear wall on the rear face of the active substance chamber is formed by a preferably reclosable cover.

By providing and arranging a cover on the rear face of the active substance chamber it can be ensured that a misplaced cover or reclosable cover does not open unintentionally, since when inserted in the implant it faces the bottom of the recess in the implant and is therefore held closed.

Preferably, the cover is secured to the active substance application insert by way of a friction fit or by means of a snap-fit or positive fit. Moreover, the cover preferably substantially forms the rear face of the active substance chamber.

In a preferred embodiment, the main body has a peripheral outer wall between the application side and the rear face, which is formed cylindrically, in particular with a circular cross section, and which surrounds the active substance chamber.

Owing to the cylindrical peripheral outer wall of the main body that can be inserted into an implant, a simple insertion into the implant along an insertion direction is possible. In other words, the active substance application insert can easily be inserted and removed again by way of a translational movement along the insertion direction.

It is also possible to provide the cylindrical shape with a circular cross section, such that it is possible to insert the active substance application insert regardless of the orientation thereof about the longitudinal axis of the main body. This longitudinal axis preferably corresponds to an insertion direction.

In a further preferred embodiment, at least one section of the outer side of the peripheral outer wall forms a friction surface as a securing means.

The use of a friction surface and therefore a friction fit for securing the inserted active substance application insert provides ease of use and also allows the removal of the active substance application insert where necessary or desired.

In a further embodiment, the peripheral outer wall forms at least one section of a peripheral active substance chamber wall between the application side and the rear face of the active substance chamber.

As a result of the fact that the peripheral outer wall forms at least one section of a peripheral active substance chamber wall, the volume of the active substance chamber and therefore a receiving volume available for the active substance can be maximised. If the peripheral outer wall forms the entire peripheral active substance chamber wall, a very simple design of the active substance application insert results, which is therefore inexpensive to produce.

In a particularly preferred embodiment, at least one section of the peripheral active substance chamber wall between the application side and the rear face of the active substance chamber is formed separately from and inside the peripheral outer wall of the main body, such that a gap is formed along this section between the outer wall of the main body and the active substance chamber wall.

This embodiment has the advantage that at least one section of the active substance chamber in the main body of the active substance application insert is spatially separated from the peripheral outer wall of the main body owing to the arrangement thereof. As a result, the main body and the active substance chamber can also be functionally separated from one another in this section. In particular, the securing means can be provided on the outer side of the peripheral outer wall of the main body in this section. Through the gap, which, like the application openings, is preferably exposed to the outside relative to the inserted active substance application insert, an elasticity of the securing means can be reliably and easily predetermined. If the securing means has a friction surface, for example, the friction force exerted on the implant by the friction surface can be adjusted via the elasticity, such that the active substance application insert is secured in place when inserted in the implant. Furthermore, adjusting the elasticity ensures a simple and unimpeded insertion and removal of the active substance application insert.

Due to the spatial separation, the section of the peripheral outer wall of the main body which is separated from the peripheral active substance chamber wall forms a preferably annular body with which the active substance application insert can be secured in the implant.

Due to this spatial separation, the peripheral outer wall of the active substance chamber is also separated at least in part from the peripheral outer wall of the main body, and is therefore relieved of any compressive forces present due to the securing means in the inserted state of the active substance application insert. As a consequence, possible damage to the active substance chamber upon insertion can be prevented, which would otherwise have an undesirable effect on the release of the active substance.

If the peripheral outer wall of the main body and the peripheral outer wall of the active substance chamber are separated over the entire region between the application side and the rear face of the active substance chamber, the two peripheral outer walls are preferably connected to one another by the rear wall of the active substance chamber. In other words, in such an embodiment they protrude as projections from the rear wall of the active substance chamber. Accordingly, the rear wall extends beyond the outer perimeter of the active substance chamber.

In a preferred embodiment, the application side is provided with a tool-engaging means for inserting and/or removing the active substance application insert.

With the tool-engaging means, the active substance application insert can be easily inserted into the implant and, in particular, can also be removed again. Accordingly, the tool-engaging means is preferably provided on the outward-facing front face of the active substance application insert or active substance chamber. Furthermore, the tool-engaging means is preferably provided centrally and/or on the outer edge of the front face.

In a particularly preferred embodiment, the tool-engaging means is formed as a recess, preferably having an internal thread.

By providing a recess as a tool-engaging means, injury to surrounding body tissue by the tool-engaging means in the implanted state can be prevented. Moreover, the tool-engaging means can be easily located and provides the user with direct feedback by engagement of the tool as to whether the tool is correctly positioned, particularly when the active substance application insert is being removed. If an internal thread is also provided, the active substance application insert can be reliably prevented from slipping during insertion into the implant and also upon withdrawal from the implant.

In a preferred embodiment, the application side has at least 4, 6, 8 or 10 and a maximum of 30 application openings, which are preferably distributed evenly over the application side.

By selecting the application openings accordingly, the dosage of the active substance can therefore be optimally selected. In addition, topical administration of the active substance can be controlled to a certain extent by way of a corresponding distribution over the application side.

Furthermore, the main body of the active substance application insert preferably has a cross section of 0.5 cm to 3 cm in size and preferably of between 1 cm and 3 cm in size.

In a further embodiment, the application openings have a minimum size of 0.5 mm or 1 mm and a maximum size of 2 mm, 3 mm or 4 mm.

The size of the application openings also facilitates optimal adjustment of the dosage of the active substance. In addition, application openings of different sizes may also be provided in an application side, in order to control the release of the active substance depending on where an application opening is located. For example, application openings in the central region of the application side can have a larger diameter since the active substance tends to diffuse in all directions from this region and therefore distributes itself more widely, while in the edge region of the application side it primarily diffuses outwardly.

In the case of asymmetric opening cross sections, the size refers to the largest opening region of an application opening.

In a preferred embodiment, the application openings are circular, oval, rectangular and/or slit-shaped.

The application openings can also perforate the application side in an evenly distributed manner. Moreover, it is possible that a mesh and/or a membrane is provided on the application side at least in sections thereof, in order to release the active substance contained in the active substance chamber into the surrounding tissue in the implanted state of the active substance application insert.

In a preferred embodiment, the active substance chamber has at least one active substance, in particular an antibiotic. The active substance is present in the form of a solid, beads, a granulate and/or a gel, which fills the active substance chamber at least in part.

Thus, the at least one active substance can be received in the active substance chamber in a variety of ways. However, it is preferably present in such a way that it is not only released by the narrowing of the cross section of the application openings over a period of time, but even in a form, for example with excipients, that results in a slower release of the active substance to the surrounding tissue.

In addition, the present invention provides an implant, in particular a joint implant and more preferably a knee joint implant, having at least one recess designed for receiving an active substance application insert according to one of the preceding claims.

Instead of an active substance application insert, it is possible to provide a geometrically corresponding body without application openings, which fills the recess of the implant if the release or administration of an active substance is not required. Such a body may have an outward-facing coated surface which facilitates the growth of surrounding tissue, for example. This is particularly advantageous if the at least one recess is provided in a region facing bone tissue in the implanted state.

The active substance application insert or a corresponding replacement body makes it possible for a permanent implant to be supplied with an active substance instead of replacement bodies or interim implants. An explantation which would otherwise be required, and the resulting immobilisation of the patient, is thereby prevented.

Furthermore, it is preferable for a maximum of four recesses to be present in the implant and it is more preferable still for one to two recesses to be present, in order to be able to receive a corresponding number of active substance application inserts. In particular, in the case of a femur component of a knee joint implant, two such recesses are provided.

BRIEF DESCRIPTION OF THE DRAWINGS

In the drawings that supplement this description, exemplary embodiments of the present invention are illustrated and described. Reference is made therein to individual features of these exemplary embodiments by way of reference numbers, wherein throughout the drawings identical reference numbers refer to features having the same design and/or function.

DETAILED DESCRIPTION OF THE PREFERRED EMBODIMENTS

Figure 1:
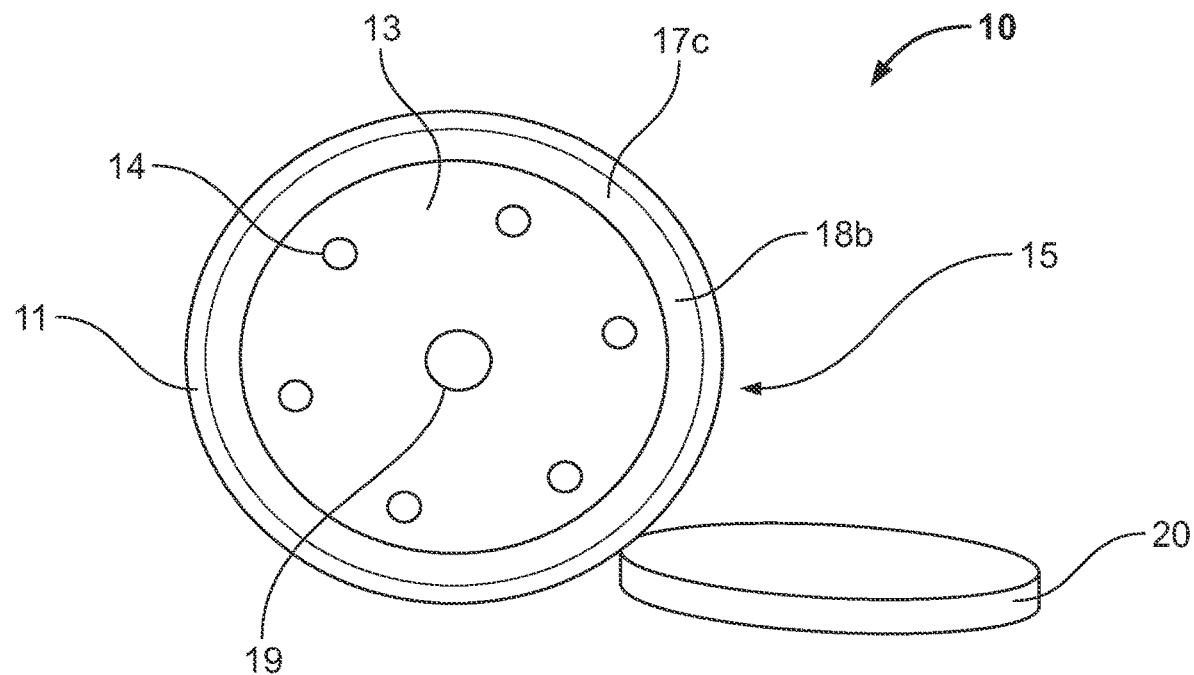
FIG. 1 illustrates a first embodiment of an active substance application insert from the application side, shown together with a removed cover, which is provided for the rear face of the active substance chamber.

On the left-hand side of FIG. 1, an active substance application insert 10 is shown from the application side 13 thereof. The application side 13 is formed as an application front wall. On the right, next to the active substance application insert 10, FIG. 1 shows a rear face 16 designed as a removable cover 20. The removable cover 20 can be pressed into an annular recess 16a of the rear face 16 (cf. FIG. 3)

such that it is held in the annular recess 16a by way of a friction fit and in this state it closes the rear face 16 of the active substance chamber 12.

In the embodiment shown, the cover 20 is provided on the rear face of the active substance application insert 10, which faces the bottom of a corresponding recess 31 in an implant 30. This effectively prevents an unintentional opening of the cover 20. As an alternative to the illustrated embodiment of an active substance application insert 10, it is also possible to provide a solid rear wall on the rear face 16, instead of a cover 20. However, a rear face 16 designed as an active substance chamber cover 20 facilitates the filling of the active substance application insert 10 with an active substance, which can be present in one of the forms described above. Alternatively, it is also possible to completely omit a rear wall on the rear face 16. With such an embodiment, the bottom of a recess 31 in an implant 30 closes the rear face 16 of the active substance application insert 10 in the inserted state thereof.

Application openings 14 are formed in the application side 13. Via these application openings 14, the active substance chamber 12 communicates with the outer side of the active substance application insert and therefore in the implanted state of the active substance application insert 10 with the body tissue of a patient. The application side can face bone tissue or soft tissue. Preferably, the active substance application insert 10 is used for a joint implant and more preferably still for a knee joint replacement (cf. FIG. 4).

The application side 13 shown in FIG. 1 has as its application openings 14 six circular through-holes. As already described above, all or some of the application openings 14 may also have a different cross section from a circular cross section. The number and/or size of the application openings can be adapted according to the desired dosage. It is generally the case that a larger number of application openings 14 and/or an enlargement of the application openings 14 allows the dosage of an active substance contained in the active substance chamber 12 to be increased.

Furthermore, it is possible to provide a membrane, a textile material and/or a mesh in at least one section of the application side 14. In the case of a membrane and/or a textile, it is also possible to adjust in a targeted manner the permeability of the active substance from the active substance chamber 12 to the outside and/or the permeability of body fluid into the active substance chamber. The application time for the active substance can also be controlled in this way.

In the exemplary embodiment shown in FIG. 1, the active substance application insert 10 also comprises a tool-engaging means 19. In this embodiment, this is designed as a through-hole and has an internal thread. Moreover, it is clear from FIG. 3 that in this exemplary embodiment the tool-engaging means also provides a connection between the active substance chamber 12 of the active substance application insert 10 and the outer side of the active substance application insert. Thus, in this embodiment the tool-engaging means forms an application opening.

Figure 4:
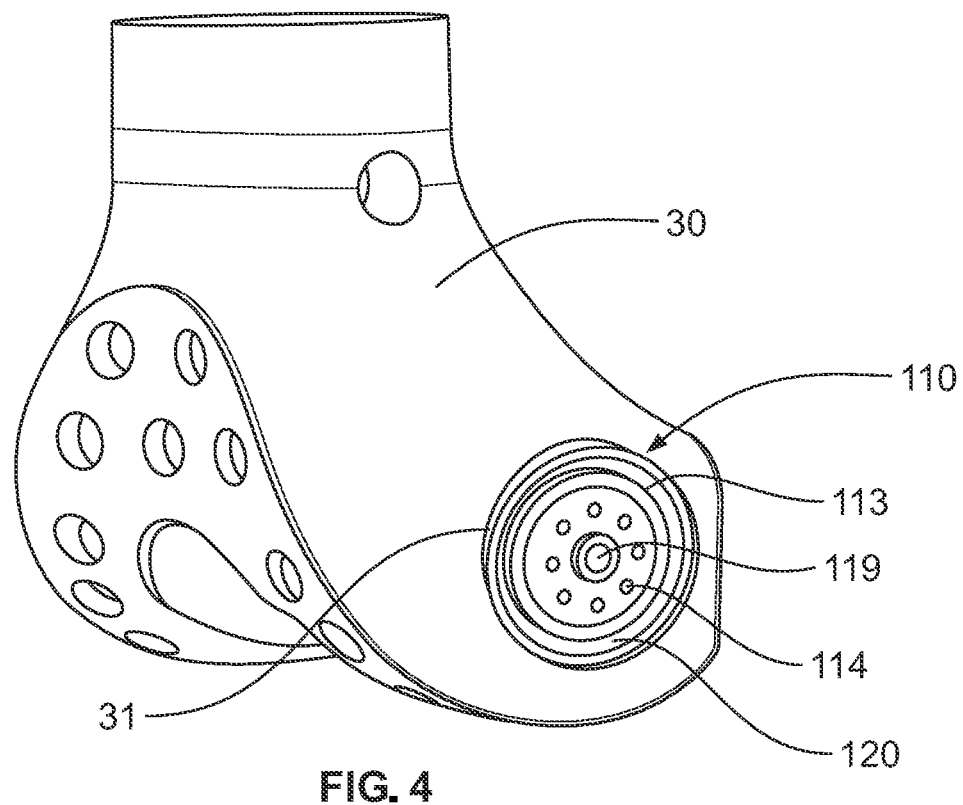
FIG. 4 illustrates an implant diagonally from the anterior thereof with an inserted active substance application insert as according to a second exemplary embodiment.

However, as can be seen in a second exemplary embodiment of an application insert 110 shown in FIG. 4, the tool-engaging means 119 can also be designed as a through-hole or blind hole which is introduced in the active substance application insert 110 in such a way that no connection is made to the active substance chamber 112. In the exemplary embodiment in FIG. 4, a central column in the active substance chamber 112 is provided for this. Thus, in this embodiment, the tool-engaging means 119 does not form an application opening 114.

Figure 2:
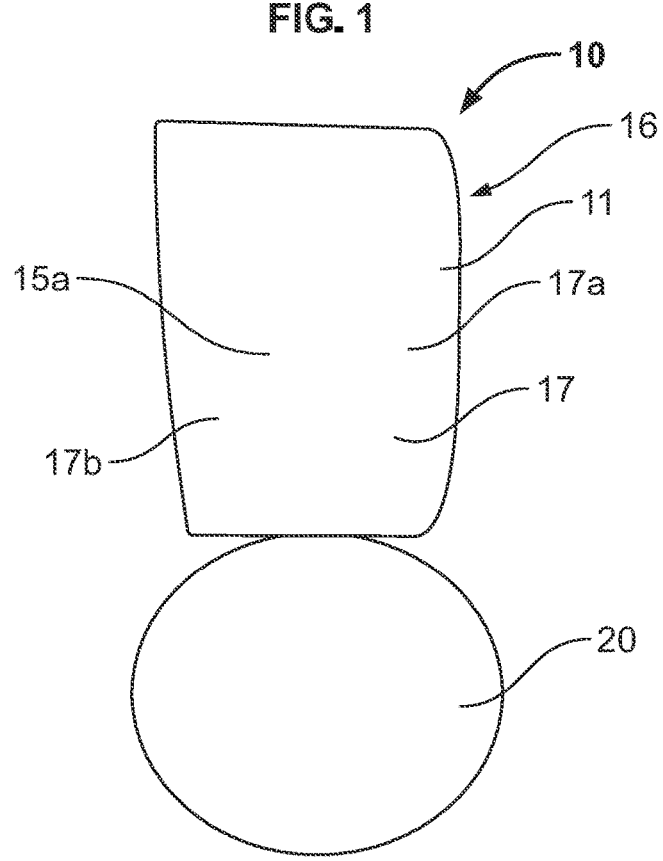
FIG. 2 is a side view of the active substance application insert from FIG. 1, also shown together with the removed cover.

In the exemplary embodiment of an active substance application insert 10 shown in FIGS. 1 and 2, the active substance chamber 12 is formed on the front face by the application side or application front wall 13 and on the rear face 16 by the cover 20. Between the application side 13 and the cover 20, the active substance chamber 12 is also delimited by a peripheral active substance chamber wall 18. Thus, the active substance chamber is defined by the application side 13 formed as the front wall, the rear face 16 designed as the active substance chamber cover 20 and the peripheral active substance chamber wall 18.

The active substance chamber wall 18 is formed in a section 17a/18a of the peripheral outer wall 17 of the main body 11. In an adjacent section 18b towards the rear face, the active substance chamber wall 18 is formed separately from the peripheral outer wall 17, however. Due to this separate formation, the active substance chamber wall 18 is arranged inside the peripheral outer wall 17 of the main body 11. As a result, there is a gap 17c between the corresponding section 17b of the peripheral outer wall 17 and the section 18b of the active substance chamber wall 18.

As can be seen from FIG. 1, for example, in section 17b the peripheral outer wall 17 is formed so as to be continuously annular due to the separation from the active substance chamber wall 18. However, it is also possible to divide in the peripheral direction the peripheral outer wall 17 in this region into outer wall sections which are separated from one another by cuts in the peripheral outer wall 17. These outer wall sections allow the elasticity of the outer wall 17 to be reduced further still. This is particularly advantageous when the securing means 15 is designed as a snap-fit. With such an embodiment, at least one part of the outer wall sections can be designed as snap-fit tabs with a locking function.

As a result of the separation of the peripheral outer wall 17 of the active substance application insert 10 and of the peripheral active substance chamber wall 18 into sections 17b and 18b and the resulting annular gap 17c, the elasticity of section 17b of the peripheral outer wall 17 can be adjusted. It is therefore possible to influence the strength of the fastening of the active substance application insert 10 in an implant 30.

As is illustrated in FIG. 1, this gap 17c of the active substance application insert 10 opens to the front on the side of the application side 13. It is possible to use this gap 17c in addition or alternatively to the tool-engaging means 19 which is formed as a recess. In this case, the recess or through-hole shown in FIG. 1 in the application side 13 can be omitted. In other words, in such an embodiment the tool-engaging means 19 is formed by the gap 17c.

In the embodiments of an active substance application insert 10 shown in the drawings, the peripheral outer wall 17 is provided with a friction surface 15a as the securing means 15. The friction surface 15a may extend over the entire peripheral outer wall 17. It is also possible for the friction surface 15a to extend over a section of the outer wall 17 that is located in sections 17a and/or 17b.

The friction surface 15a may be provided as an enlargement of the cross section on the peripheral outer wall 17 of the main body 11 and/or with a higher surface roughness than the surface of the peripheral outer wall without the friction surface 15a. The friction surface can be provided at least or only on the less elastic section 17a. In this section 17a it is possible to generate a higher friction force in order to secure the active substance application insert 10 in an implant 30 on account of the lower degree of elasticity of the friction surface 15a.

By forming the friction surface 15a in section 17b of the peripheral outer wall 17 of the active substance application insert 10, the elasticity 17b can be selected in a broader area, however, such that when inserted into a corresponding recess 31 of an implant 30 the active substance application insert 10 can be inserted more easily and then fixed in this recess 31. Moreover, the elasticity of section 17a and/or 17b can be selected such that removing the active substance application insert 10 from the recess 31 of an implant 30 is also possible without excessive effort.

The elasticity is preferably selected such that a manual insertion and/or removal is possible. At least in the case of a removal it is preferable for a tool to be used which engages with a tool-engaging means 19 of the active substance application insert.

Furthermore, as a result of the separation of the active substance chamber wall 18 and the outer wall 17 of the main body 11, the influence of compressive forces created by the insertion of the active substance application insert 10 into an implant 30 is minimised on the side of the active substance chamber 12. For a start, this prevents possible damage to the active substance chamber 12. In addition, distortion of the application openings 14 cannot occur on the application side 13 and therefore an intended dosage cannot be influenced in an undesired way. This is particularly advantageous in the case of application openings 14 of a size in the lower part of the range indicated above.

Figure 3:
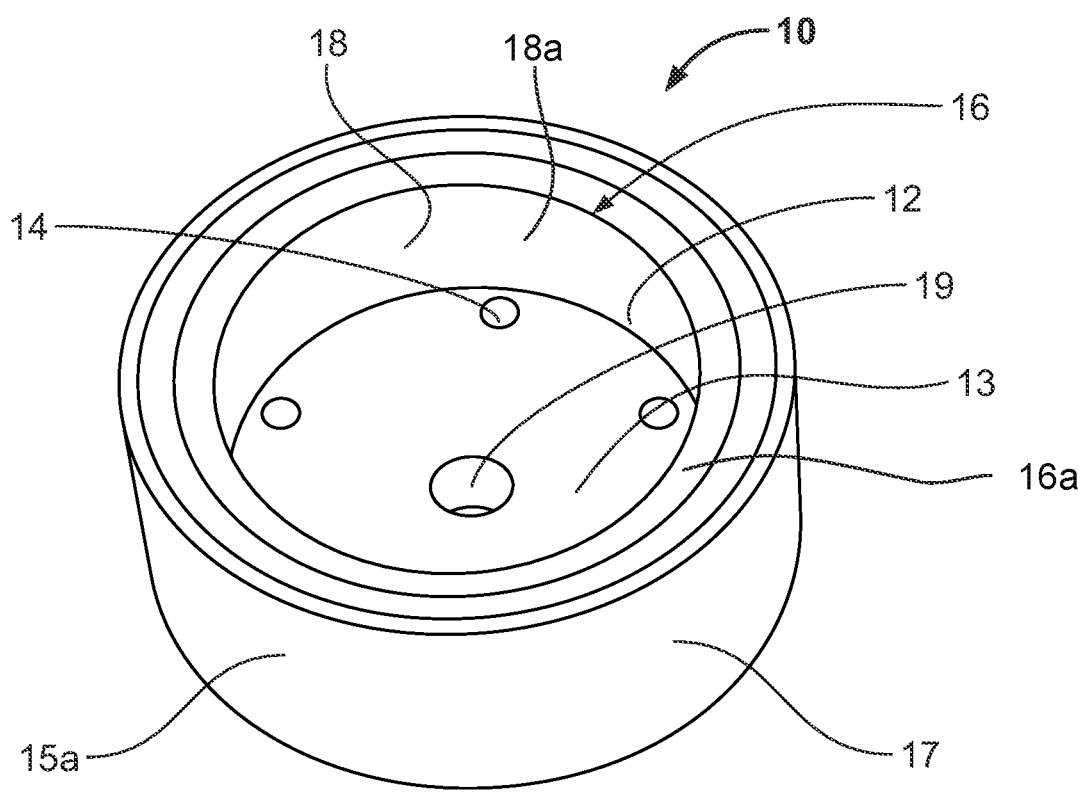
FIG. 3 is a view into the active substance chamber of the active substance application insert of FIG. 1, viewed diagonally from the rear face of the active substance application insert.

Even if the elastic section 17b of the peripheral outer wall 17 in the exemplary embodiment of an active substance application insert 10 shown in FIGS. 1 to 3 is arranged on the side of the application side 13, it is also possible to provide this elastic section 17b on the side of the rear face. With such an embodiment, in the inserted state of the active substance application insert 10 the annular gap 17c therefore faces the bottom of a recess 31 in an implant 30.

As illustrated in FIGS. 1 to 4, the peripheral outer wall 17 of the active substance application insert 10, 110 is cylindrical. In addition to the circular-cylindrical shape shown, other cylindrical shapes are also conceivable, as already stated above. However, the cylindrical shape shown simplifies the insertion of the active substance application insert 10 since the orientation thereof about its longitudinal axis, which extends from the front face to the rear face of the active substance application insert 10, does not have to be taken into consideration.

As can also be seen from the side view of the active substance application insert 10 in FIG. 2, the rear face 16 or the active substance chamber cover 20 is arranged perpendicularly to the longitudinal axis of the active substance application insert 10. The application side 13, however, has an angle to the longitudinal axis. As a result of this arrangement, which is inclined with respect to the longitudinal axis, the application side 13 is adapted to the outer contour of the implant 30 into which the active substance application insert 10 is to be inserted. Depending on the outer contour of the implant 30, the application side 13 may also have a more complex shape, such as a curved shape, for example. As a result of adapting the shape and/or orientation of the application side 13 to the outer contour of an implant 30 in this way, injury to surrounding tissue can in particular be prevented.

In FIG. 4, a very limited adaptation of the application side 13 of a second embodiment of the active substance application insert 110 to the outer contour of the illustrated knee joint implant 30 has been carried out. Furthermore, in contrast to the embodiment of the active substance application insert 10 shown in FIGS. 1 to 3, the application side 113 of the active substance application insert 110 is designed with its application openings 114 as a removable cover 120. As a consequence, the active substance chamber can be replaced or refilled without the active substance application insert 110 having to be removed for this.

The active substance application inserts 10, 110 are preferably inserted in permanent implants 30. Yet it is also possible to use an active substance application insert 10, 110 as according to the invention with an interim prosthesis. However, particularly in the case of permanently or definitively inserted implants there is the advantage that an explantation of the implant is generally avoided, even in the event of an infection.

If the present invention is used with a knee joint implant, it is preferable for an active substance application insert as according to the invention to be provided on the medial and/or lateral side of the femur components of such an implant. With this positioning, the application side faces soft tissue, as a consequence of which the active substance disperses quickly and reliably into the surroundings of the implant.

LIST OF REFERENCE NUMBERS 10, 110 Active substance application insert
11 Main body
12 Active substance chamber
13, 113 Application side
14, 114 Application openings
15 Securing means
15a Friction surface
16 Rear face
16a Annular recess
17 Peripheral outer wall
17a Outer wall section as chamber wall
17b Outer wall section separated from the active substance chamber wall
17c Gap
18 Peripheral active substance chamber wall
18b Separated section of the active substance chamber wall
19, 119 Tool-engaging means
20, 120 Active substance chamber cover
30 Implant
31 Recess for receiving an active substance application insert

The invention claimed is:

1. An active substance application insert for an implant, comprising:
a main body,
an active substance chamber formed in the main body,
a peripheral active substance wall that extends around a perimeter of the active substance chamber,
an application side which forms a front face of the active substance chamber, wherein the application side faces bone tissue or soft tissue and has a plurality of application openings, and
a securing means configured to detachably secure the main body in the implant,
wherein in a state in which the main body is inserted into the implant, the application side faces outwards relative to the implant, such that the application openings connect the active substance chamber to the environment outside of the implant when the implant is implanted in a body of a patient,
wherein on the side opposite the application side a rear wall is formed, which forms a rear face of the active substance chamber and which faces the implant in the inserted state,
wherein at least one section of the rear wall on the rear face of the active substance chamber is formed by a reclosable cover,
wherein the main body has a peripheral outer wall between the front face and the rear face, which extends around a perimeter of the active substance application insert, and
wherein at least one section of the peripheral active substance wall between the application side and the rear face of the active substance chamber is formed separately from and inside the peripheral outer wall of the main body, such that an annular gap is formed along this section between the peripheral outer wall of the main body and the peripheral active substance wall.

2. The active substance application insert according to claim 1, wherein
the securing means is formed by at least one section of the outer side of the peripheral outer wall forming a friction surface.

3. The active substance application insert according to claim 1,
wherein the peripheral outer wall forms at least one section of the peripheral active substance chamber wall between the application side and the rear face of the active substance chamber.

4. The active substance application insert according to claim 1, wherein
the application side is provided with a tool-engaging means for inserting and/or removing the active substance application insert.

5. The active substance application insert according to claim 1, wherein the application side has at least 4, 6, 8 or 10 and a maximum of 30 application openings.

6. The active substance application insert of claim 5, in which the application openings are distributed evenly over the application side.

7. The active substance application insert according to claim 1, wherein
the application openings have a minimum size of 0.5 mm or 1 mm and a maximum size of 2 mm, 3 mm or 4 mm.

8. The active substance application insert according to claim 1, wherein the application openings are circular, oval, rectangular and/or slit-shaped.

9. The active substance application insert according to claim 1, having at least one active substance in the form of a solid, beads, a granulate and/or a gel, which fills the active substance chamber at least in part.

10. The active substance application insert according to claim 9, having an active substance that is an antibiotic.

11. An implant system, the implant system comprising:
an implant; and
an active substance application insert, wherein the implant comprises a cavity corresponding to a shape of the active substance application insert, the active substance application insert comprising:
a main body,
an active substance chamber formed in the main body, wherein the active substance chamber is arranged inside a peripheral outer wall,
a peripheral active substance wall that extends around a perimeter of the active substance chamber,
an application side which forms a front face of the active substance chamber, wherein the application side faces bone tissue or soft tissue and has a plurality of application openings, and
a securing means configured to detachably secure the main body in the implant,
wherein in a state in which the main body is inserted into the implant, the peripheral outer wall contacts a periphery of the cavity and the front face is coplanar with a surface of the implant,
and in the state in which the main body is inserted into the implant, the application side faces outwards relative to the implant, such that the application openings connect the active substance chamber to the environment outside of the implant when the implant is implanted in a body of a patient,
wherein the peripheral outer wall is between the front face and a rear face of the active substance chamber, which extends around a perimeter of the active substance application insert, and
wherein at least one section of the peripheral active substance wall between the application side and the rear face of the active substance chamber is formed separately from and inside the peripheral outer wall of the main body, such that an annular gap is formed along this section between the peripheral outer wall of the main body and the peripheral active substance wall.

12. The implant system according to claim 11, wherein the securing means is formed by at least one section of the outer side of the peripheral outer wall forming a friction surface.

13. The implant system according to claim 11,
wherein the peripheral outer wall forms at least one section of a peripheral active substance chamber wall between the application side and the rear face of the active substance chamber.

14. The implant system according to claim 11, wherein the application side is provided with a tool-engaging means for inserting and/or removing the active substance application insert.

* * * * *